United States Patent [19]
Renner et al.

[11] Patent Number: 5,811,299
[45] Date of Patent: Sep. 22, 1998

[54] METHODS FOR THE ACTIVATION OF PROLIFERATION OF ANIMAL CELLS

[76] Inventors: Wolfgang A. Renner, Im Marcoup 2, CH-3286 Muntelier; Hans M. Eppenberger, Wiesenweg 5, CH-8116 Würenlos; James E. Bailey, Winkelwiese 6, CH-8001 Zürich, all of Switzerland

[21] Appl. No.: 385,142

[22] Filed: Feb. 7, 1995

[30] Foreign Application Priority Data

Feb. 8, 1994 [CH] Switzerland ............... 363/94

[51] Int. Cl.[6] ............... C12N 5/06; C12N 5/10
[52] U.S. Cl. ............ 435/325; 435/358; 435/375
[58] Field of Search ............. 435/69.1, 240.1, 435/240.2, 240.3, 240.31, 320.1, 948, 325, 358, 375; 935/6, 9, 10, 11, 14, 23, 27, 34, 36, 66, 70, 71

[56] References Cited

U.S. PATENT DOCUMENTS 5,122,469  6/1992  Mather et al. ............... 435/383

FOREIGN PATENT DOCUMENTS

WO 93/08267  4/1993  WIPO .

OTHER PUBLICATIONS

Hatzimanikatis et al., "A Mathematial Model for the G1/S Transition of the Mammalian Cell Cycle," *Biotechnology Letters,* 17: 669–674 (1995).

Jacobs, "Control of the Cell Cycle," *Developmental Biology,* 153: 1–15 (1992).

Lee et al., "Two–Dimensional Electrophoresis of Proteins as a Tool in the Metabolic Engineering of Cell Cycle Regulation," *Biotechnology and Bioengineering,* 50: 336–340 (1996).

McGill et al., "Cell cycle control mechanisms and their role in cardiac growth," *Cardiovascular Research,* 30: 557–569 (1995).

Matsuda et al., "Purification and Characterization of a Novel Growth Factor (FF–GF) Synthesized by a Rat Hepatoma Cell Line, FF101", *BBRC 189,* No. 2:654–661(1992).

Shive et al., "Development of a Chemically Defined Serum–and Protein–Free Medium for Growth of Human Peripheral Lymphoytes", *Proc. Natl. Acad. Sci.* 83:9–13 (Jan. 1986).

Skreb et al., "Differentiation and Growth of Rat Egg–Cylinders Cultured in Vitro in a Serum–Free and Protein–Free Medium", *Int. J. Dev. Biol.* 37:151–154 (1993).

Sato et al. (1994) Specific cell types and their requirements. In Basic Cell Culture: A Practical Approach. J.M. Davis ed., IRL Press, Oxford, pp. 181–222.

Alberts et al. (1994) Molecular Biology of the Cell, Third Edition, Garland, New York, p. 892.

*Primary Examiner*—George C. Elliott
*Assistant Examiner*—Robert Schwartzman
*Attorney, Agent, or Firm*—Marshall, O'Toole, Gerstein, Murray & Borun

[57] ABSTRACT

Cell cultures are described which proliferate in a serum- and protein-free environment and which are characterized by the circumstance that the concentration of at least one cell-cycle-regulatory protein is increased during at least one period of the cell-cycle. Methods for the production of such cell cultures are presented. With these methods cell lines can be transferred to serum- and protein-free growth that are already in use in a production process which, prior to the use of these methods, requires serum or proteins added to the basal medium.

28 Claims, 5 Drawing Sheets

CHO K1:cycE

CHO K1

CHO K1:E2F-1

CHO K1:pRc

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1680 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GTGCTCACCC    GGCCCGGTGC    CACCCGGGTC    CACAGGGATG    CGAAGGAGCG    GGACACCATG         60

AAGGAGGACG    GCGGCGCGGA    GTTCTCGGCT    CGCTCCAGGA    AGAGGAAGGC    AAACGTGACC        120

GTTTTTTTGC    AGGATCCAGA    TGAAGAAATG    GCCAAAATCG    ACAGGACGGC    GAGGGACCAG        180

TGTGGGAGCC    AGCCTTGGGA    CAATAATGCA    GTCTGTGCAG    ACCCCTGCTC    CCTGATCCCC        240

ACACCTGACA    AAGAAGATGA    TGACCGGGTT    TACCCAAACT    CAACGTGCAA    GCCTCGGATT        300

ATTGCACCAT    CCAGAGGCTC    CCCGCTGCCT    GTACTGAGCT    GGGCAAATAG    AGAGGAAGTC        360

TGGAAAATCA    TGTTAAACAA    GGAAAAGACA    TACTTAAGGG    ATCAGCACTT    TCTTGAGCAA        420

CACCCTCTTC    TGCAGCCAAA    AATGCGAGCA    ATTCTTCTGG    ATTGGTTAAT    GGAGGTGTGT        480

GAAGTCTATA    AACTTCACAG    GGAGACCTTT    TACTTGGCAC    AAGATTTCTT    TGACCGGTAT        540
```

-continued

| | | | | | |
|---|---|---|---|---|---|
|ATGGCGACAC|AAGAAAATGT|TGTAAAAACT|CTTTTACAGC|TTATTGGGAT|TTCATCTTTA 600|
|TTTATTGCAG|CCAAACTTGA|GGAAATCTAT|CCTCCAAAGT|TGCACCAGTT|TGCGTATGTG 660|
|ACAGATGGAG|CTTGTTCAGG|AGATGAAATT|CTCACCATGG|AATTAATGAT|TATGAAGGCC 720|
|CTTAAGTGGC|GTTTAAGTCC|CCTGACTATT|GTGTCCTGGC|TGAATGTATA|CATGCAGGTT 780|
|GCATATCTAA|ATGACTTACA|TGAAGTGCTA|CTGCCGCAGT|ATCCCCAGCA|AATCTTTATA 840|
|CAGATTGCAG|AGCTGTTGGA|TCTCTGTGTC|CTGGATGTTG|ACTGCCTTGA|ATTTCCTTAT 900|
|GGTATACTTG|CTGCTTCGGC|CTTGTATCAT|TTCTCGTCAT|CTGAATTGAT|GCAAAGGTT 960|
|TCAGGGTATC|AGTGGTGCGA|CATAGAGAAC|TGTGTCAAGT|GGATGGTTCC|ATTTGCCATG 1020|
|GTTATAAGGG|AGACGGGGAG|CTCAAAACTG|AAGCACTTCA|GGGGCGTCGC|TGATGAAGAT 1080|
|GCACACAACA|TACAGACCCA|CAGAGACAGC|TTGGATTTGC|TGGACAAAGC|CCGAGCAAAG 1140|
|AAAGCCATGT|TGTCTGAACA|AAATAGGGCT|TCTCCTCTCC|CCAGTGGGCT|CCTCACCCCG 1200|
|CCACAGAGCG|GTAAGAAGCA|GAGCAGCGGG|CCGGAAATGG|CGTGACCACC|CCATCCTTCT 1260|
|CCACCAAAGA|CAGTTGCGCG|CCTGCTCCAC|GTTCTCTTCT|GTCTGTTGCA|GCGGAGGCGT 1320|
|GCGTTTGCTT|TTACAGATAT|CTGAATGGAA|GAGTGTTTCT|TCCACAACAG|AAGTATTTCT 1380|
|GTGGATGGCA|TCAAACAGGG|CAAAGTGTTT|TTTATTGAAT|GCTTATAGGT|TTTTTTTAAA 1440|
|TAAGTGGGTC|AAGTACACCA|GCCACCTCCA|GACACCAGTG|CGTGCTCCCG|ATGCTGCTAT 1500|
|GGAAGGTGCT|ACTTGACCTA|AAGGACTCCC|ACAACAACAA|AAGCTTGAAG|CTGTGGAGGG 1560|
|CCACGGTGGC|GTGGCTCTCC|TCGCAGGTGT|TCTGGGCTCC|GTTGTACCAA|GTGGAGCAGG 1620|
|TGGTTGCGGG|CAAGCGTTGT|GCAGAGCCCA|TAGCCAGCTG|GGCAGGGGC|TGCCCTCTCC 1680|

( 2 ) INFORMATION FOR SEQ ID NO:2:

( i ) SEQUENCE CHARACTERISTICS:
        ( A ) LENGTH: 2517 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
|GGAATTCCGT|GGCCGGGACT|TTGCAGGCAG|CGGCGGCCGG|GGGCGGAGCG|GGATCGAGCC 60|
|CTCGCCGAGG|CCTGCCGCCA|TGGGCCCGCG|CCGCCGCCGC|CGCCTGTCAC|CCGGGCCGCG 120|
|CGGGCCGTGA|GCGTCATGGC|CTTGGCCGGG|GCCCTGCGG|GCGGCCCATG|CGCGCCGGCG 180|
|CTGGAGGCCC|TGCTCGGGGC|CGGCGCGCTG|CGGCTGCTCG|ACTCCTCGCA|GATCGTCATC 240|
|ATCTCCGCCG|CGCAGGACGC|CAGCGCCCCG|CCGGCTCCCA|CCGGCCCCGC|GGCGCCCGCC 300|
|GCCGGCCCCT|GCGACCCTGA|CCTGCTGCTC|TTCGCCACAC|CGCAGGCGCC|CCGGCCCACA 360|
|CCCAGTGCGC|CGCGGCCCGC|GCTCGGCCGC|CCGCCGGTGA|AGCGGAGGCT|GGACCTGGAA 420|
|ACTGACCATC|AGTACCTGGC|CGAGAGCAGT|GGGCCAGCTC|GGGGCAGAGG|CCGCCATCCA 480|
|GGAAAAGGTG|TGAAATCCCC|GGGGAGAAG|TCACGCTATG|AGACCTCACT|GAATCTGACC 540|
|ACCAAGCGCT|TCCTGGAGCT|GCTGAGCCAC|TCGGCTGACG|GTGTCGTCGA|CCTGAACTGG 600|
|GCTGCCGAGG|TGCTGAAGGT|GCAGAAGCGG|CGCATCTATG|ACATCACCAA|CGTCCTTGAG 660|
|GGCATCCAGC|TCATTGCCAA|GAAGTCCAAG|AACCACATCC|AGTGGCTGGG|CAGCCACACC 720|
|ACAGTGGGCG|TCGGCGGACG|GCTTGAGGGG|TTGACCCAGG|ACCTCCACA|GCTGCAGGAG 780|
|AGCGAGCAGC|AGCTGGACCA|CCTGATGAAT|ATCTGTACTA|CGCAGCTGCG|CCTGCTCTCC 840|

-continued

| | | | | | | |
|---|---|---|---|---|---|---|
| GAGGACACTG | ACAGCCAGCG | CCTGGCCTAC | GTGACGTGTC | AGGACCTTCG | TAGCATTGCA | 900 |
| GACCCTGCAG | AGCAGATGGT | TATGGTGATC | AAAGCCCCTC | CTGAGACCCA | GCTCCAAGCC | 960 |
| GTGGACTCTT | CGGAGAACTT | TCAGATCTCC | CTTAAGAGCA | AACAAGGCCC | GATCGATGTT | 1020 |
| TTCCTGTGCC | CTGAGGAGAC | CGTAGGTGGG | ATCAGCCCTG | GGAAGACCCC | ATCCCAGGAG | 1080 |
| GTCACTTCTG | AGGAGGAGAA | CAGGGCCACT | GACTCTGCCA | CCATAGTGTC | ACCACCACCA | 1140 |
| TCATCTCCCC | CCTCATCCCT | CACCACAGAT | CCCAGCCAGT | CTCTACTCAG | CCTGGAGCAA | 1200 |
| GAACCGCTGT | TGTCCCGGAT | GGGCAGCCTG | CGGGCTCCCG | TGGACGAGGA | CCGCCTGTCC | 1260 |
| CCGCTGGTGG | CGGCCGACTC | GCTCCTGGAG | CATGTGCGGG | AGGACTTCTC | CGGCCTCCTC | 1320 |
| CCTGAGGAGT | TCATCAGCCT | TTCCCCACCC | CACGAGGCCC | TCGACTACCA | CTTCGGCCTC | 1380 |
| GAGGAGGGCG | AGGGCATCAG | AGACCTCTTC | GACTGTGACT | TTGGGGACCT | CACCCCCCTG | 1440 |
| GATTTCTGAC | AGGGCTTGGA | GGGACCAGGG | TTTCCAGAGT | AGCTCACCTT | GTCTCTGCAG | 1500 |
| CCCTGGAGCC | CCCTGTCCCT | GGCCGTCCTC | CCAGCCTGTT | TGGAAACATT | TAATTTATAC | 1560 |
| CCCTCTCCTC | TGTCTCCAGA | AGCTTCTAGC | TCTGGGGTCT | GGCTACCGCT | AGGAGGCTGA | 1620 |
| GCAAGCCAGG | AAGGGAAGGA | GTCTGTGTGG | TGTGTATGTG | CATGCAGCCT | ACACCCACAC | 1680 |
| GTGTGTACCG | GGGGTGAATG | TGTGTGAGCA | TGTGTGTGTG | CATGTACCGG | GGAATGAAGG | 1740 |
| TGAACATACA | CCTCTGTGTG | TGCACTGCAG | ACACGCCCCA | GTGTGTCCAC | ATGTGTGTGC | 1800 |
| ATGAGTCCAT | CTCTGCGCGT | GGGGGGGCTC | TAACTGCACT | TTCGGCCCTT | TTGCTCGTGG | 1860 |
| GGTCCCACAA | GGCCCAGGGC | AGTGCCTGCT | CCCAGAATCT | GGTGCTCTGA | CCAGGCCAGG | 1920 |
| TGGGGAGGCT | TTGGCTGGCT | GGGCGTGTAG | GACGGTGAGA | GCACTTCTGT | CTTAAAGGTT | 1980 |
| TTTTCTGATT | GAAGCTTTAA | TGGAGCGTTA | TTTATTTATC | GAGGCCTCTT | TGGTGAGCCT | 2040 |
| GGGGAATCAG | CAAAAGGGGA | GGAGGGGTGT | GGGGTTGATA | CCCCAACTCC | CTCTACCCTT | 2100 |
| GAGCAAGGGC | AGGGGTCCCT | GAGCTGTTCT | TCTGCCCCAT | ACTGAAGGAA | CTGAGGCCTG | 2160 |
| GGTGATTTAT | TTATTGGGAA | AGTGAGGGAG | GGAGACAGAC | TGACTGACAG | CCATGGGTGG | 2220 |
| TCAGATGGTG | GGGTGGGCCC | TCTCCAGGGG | GCCAGTTCAG | GGCCCAGCTG | CCCCCCAGGA | 2280 |
| TGGATATGAG | ATGGGAGAGG | TGAGTGGGGG | ACCTTCACTG | ATGTGGGCAG | GAGGGGTGGT | 2340 |
| GAAGGCCTCC | CCCAGCCCAG | ACCCTGTGGT | CCCTCCTGCA | GTGTCTGAAG | CGCCTGCCTC | 2400 |
| CCCACTGCTC | TGCCCCACCC | TCCAATCTGC | ACTTTGATTT | GCTTCCTAAC | AGCTCTGTTC | 2460 |
| CCTCCTGCTT | TGGTTTTAAT | AAATATTTTG | ATGACGTTAA | AAAAAGGAAT | TCGATAT | 2517 |

METHODS FOR THE ACTIVATION OF PROLIFERATION OF ANIMAL CELLS

BACKGROUND OF THE INVENTION

Cultures of genetically engineered animal cells are currently used to produce posttranslationally modified and physiologically active proteins for use as pharmaceutic agents. These cell lines are usually derived from tumor cells and used for this purpose because of their ability to proliferate infinitely. Cell culture for pharmaceutical protein production is an expensive, slow process due to the complex media required and the slow kinetics of cell reproduction. Animal cells usually require mitogenic stimulation to proliferate. This mitogenic stimulation is exerted by growth factors, which are supplied to the medium either as purified proteins or by the addition of animal blood sera. The latter causes a number of problems but nevertheless is used currently in biotechnological manufacturing processes employing animal cells. Fetal blood sera carry a risk of contamination by viruses, mycoplasma and prions. The screening of animal blood sera for viruses and mycoplasma is feasible but expensive and complicated. It is possible to inactivate these contaminants by heating the serum. However this is not true for any prion contaminants. Prions are the pathogens of the human diseases Kuru and Creutzfeld-Jacob-syndrome, the sheep disease Scrapie and the bovine spongiform encephalitis (BSE, "mad cow disease"). These diseases are fatal and characterized by the breakdown of the central nervous system. Since the pathogen (PrP) is most likely a protein, its potential presence represents a significant problem for cell culture. Since the PrP protein is highly heat stable, it can not be inactivated in serum without inactivating the important growth factors at the same time. The present mode of action of legal authorities to prevent any risk of PrP contamination is the restriction of sera to sources where no cases of BSE have occurred yet. The risk of infectious contamination is not the only problem connected to the use of blood sera. Residual traces of other non-infectious proteins are considered potential sources of allergenic reactions in the patient.

Due to the presence of serum the cell culture process operation and downstream processing are difficult. First, process consistency is complicated since varying serum qualities can lead to different growth and production patterns. Food, age and weather conditions as well as health of the cattle influence the quality of the serum. In downstream processing the presence of relatively large quantities of numerous serum proteins in the product stream makes the purification of the desired product difficult.

Ethical questions and concern for animal protection have to be mentioned in this context. Therapeutic proteins may be required in relatively high amounts. 10,000 liter reactors are not unusual for the culture of mammalian cells, and the media used in these processes. are usually supplemented with 2–10% serum. This leads to a requirement of a few hundred liters of animal blood serum per batch. Finally, financial concerns should be mentioned. The use of serum increases the cost of a production process, first by the direct costs for the serum and second by the indirect costs which are caused by extensive quality control work and more complicated bioreactor and/or downstream processing operations.

Considering all the above-mentioned problems, one can easily draw the conclusion that animal blood sera should be removed from biotechnological processes wherever possible. One way to accomplish this goal is to add particular, purified growth factors, produced in recombinant microbial processes, to the cell culture medium. Another possible way is selection of mutants that can grow in a serum- and protein-free environment. The disadvantage of the second approach is its long duration (several months) and the fact that both the genotype and phenotype of the resulting cell line are unpredictable. Glycosylation patterns, for example, might be different in such derived cell lines. Therefore a rational and straightforward method was developed here to convert serum-dependent cell lines to serum-free and protein-free growth. The approach that has been chosen includes the genetic engineering of the controls by which the progression through the cell-cycle is regulated.

DESCRIPTION OF PRIOR ART

Growth factors regulate the growth and differentiation of animal cells. They bind to specific receptors on the surface of the cell and induce an intracellular signal cascade which leads to DNA synthesis and finally to the division of the cell. Based on the present study, an important step herein seems to be the induction of the synthesis of cell-cycle regulatory proteins. A group of these proteins was called cyclins because of their cyclic appearance in the cell-cycle. It is believed that these proteins regulate the progression through the cell-cycle as regulatory subunits in complex with kinases (cyclin dependent kinases, or cdk's). The formation of a complex of the p34 cdc2 kinase (also called p34) with cyclin B and subsequent dephosphorylation of this complex, for example, was recognized to be the determining step for the entry into mitosis (Jacobs, T. Dev. Biol. 153, 1–15 (1992)). Cyclin C, Cyclin D1, D2 and D3 as well as Cyclin E appear during the G1 phase of the cell-cycle. It is believed that these proteins regulate the entry into the cell-cycle. In order to demonstrate the importance of the expression of cyclins for proliferation, experiments were carried out in which cyclins were expressed constitutively in animal cells. The behavior of these cells after reduction of the serum concentration was studied. In none of the cases reported so far have the cells continued to proliferate after serum removal. Not even in medium still containing serum (at 0.1 volume %) could long-term proliferation of the cells be observed. It was therefore suggested that the expression of cyclin E is only one of several events that are necessary for the entry into the cell-cycle and associated proliferation of the cells, (Ohtsubo, M. and Roberts, J. M: Science 259, 1908–1912 (1993)). Similar experiments were carried out with the transcription factor E2F. Also in these experiments no continuous proliferation could be observed (Johnson, D. G., Schwarz, J. K., Cress, W. D. and Nevins, J. R. Nature 349–52 (1993)).

Although animal cells are currently used for the production of pharmaceutical substances, the cell culture systems using animal blood serum are highly unsatisfactory. The high risk of contamination (by viruses, mycoplasma, prions and allergenic proteins), the problematic product recovery in a high-protein background, varying quality of the serum, the high costs as well as ethical concerns and concerns of animal protection are clear motivations (or reasons) against a further use of serum or any animal protein as medium additives.

Efforts to establish serum-free growing cell lines by spontaneous or induced random mutations are sometimes successful (Gandor, C. Dissertation ETH No. 10087). These cell lines seem to be growth regulated by an autocrine mechanism. It can be assumed that beneficial properties of a production cell line can be lost in the process of selection, which usually takes months. Mutations in the product gene or in a gene which codes for processing enzymes might have consequences. Such consequences can only be avoided by a clearly defined, relatively rapid process for obtaining a modified cell which grows rapidly in medium-free protein.

In basic science research, different experiments have been conducted which sought to demonstrate the importance of cyclin expression for the passage through the cell-cycle. These experiments did not raise hope that one could use cell-cycle regulatory genes for the production of serum- and protein-free growing cell lines. In no earlier reports was a cell line obtained that had the ability for sustained cell division and growth after reduction of the serum content in the medium (Ohtsubo, M. and Roberts, J. M. Science 259, 1908–1912 (1993), Johnson, D. G., Schwarz, J. K. Cress, W. D. and Nevins, J. R.

Nature 365, 349–352 (1993)).

SUMMARY OF THE INVENTION

The aim of the invention is the production of novel animal cell cultures, particularly mammalian cell cultures, by a process which leads to an increase, at least transiently in the cell-cycle, of the intracellular concentration of a cell-cycle regulatory protein. This process enables the duplication of the animal cell in a serum-free environment. Surprisingly the inventors were successful in culturing CHO K1 cells in a completely serum-free and protein-free medium after the transfection of these cells with an expression vector for cyclin E. This cell line seems to be completely growth factor-independent; it grows at extremely low cell densities. The disadvantages that arise by the conventional selection of serum-free growing clones can be circumvented by the method described here. The process is a clearly defined procedure which takes about four weeks.

The object of the invention presented here was the production of animal cell cultures with the ability to proliferate in serum-free and protein-free media, characterized by an increased intracellular concentration of a cell-cycle regulatory protein and/or by the presence of cells containing at least one exogenous nucleic acid sequence coding for a cell-cycle regulatory protein.

Further objects of the invention presented here are methods for the production of such cell lines, the use of nucleic acid sequences as DNA (genomic as well as cDNA) and / or mRNA, which is coding for a cell-cycle regulatory protein, or the use of cell-cycle regulatory protein which was produced by other methods, in order to increase, at least transiently in the cell-cycle the intracellular concentration of the protein mentioned above. A further object of the invention is a method using such cell cultures for the production of pharmaceutical products such as therapeutics, diagnostics, vaccines and substances for use in biological or medical research and development.

DESCRIPTION OF THE PREFERRED EMBODYMENTS

Figure 1:
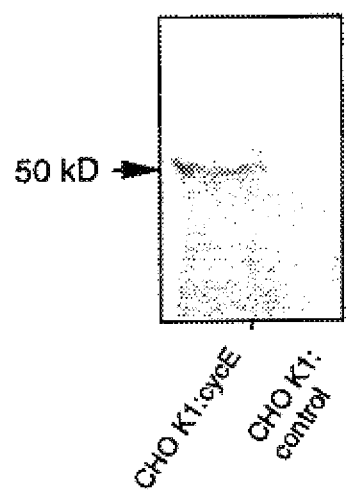
FIG. 1 shows a Western blot analysis of cyclin E over-expressing CHO K1 cells, as well as control cells which were transfected with the empty expression vector.

The intracellular concentration of cell-cycle regulatory proteins can be increased for example by the insertion of nucleic acid sequences coding for a cell-cycle regulatory protein into a different DNA environment than normally found in this particular cell type. This leads to at least a transient increase of the concentration of the cell-cycle regulatory protein in the cells during the cell-cycle.

Examples of nucleic acid sequences are the CDNA of human cyclin E (see SEQ ID NO:1, EMBL No. M73812) and the cDNA sequence of the human transcription factor E2F-1 (see SEQ ID NO:2, EMBL No. M96577), or other sequences with the property to increase the concentration of cell-cycle regulatory proteins and thereby allowing animal cells to proliferate in a serum-free and protein-free medium.

Nucleic acid sequences are either synthetically produced nucleic acid sequences or fragments of naturally occurring nucleic acid sequences as well as modifications of naturally occurring nucleic acid sequences with the properties mentioned above, i.e. genomic DNA, CDNA, mRNA as well as their modified counterparts.

To further specify the cell-cycle regulatory proteins, such proteins are meant whose primary structure is encoded by deoxyribonucleic acid (DNA) codons in a DNA sequence which directs the synthesis of an amino acid chain which can be posttranslationally modified or not (i.e. phosphorylation, glycosylation etc.). Moreover a cell-cycle regulatory protein is defined by its ability to influence progression through cell-cycle check-points. One group of such proteins include all those which interact with the retinoblastoma protein; i.e. transcription factors of the E2F family, cyclin-dependent kinases (cdk's) and cyclins, as well as those which generally suppress the inhibitory action of the retinoblastoma protein.

The nucleic acid sequences are inserted into the animal cells in vectors which allow the transcription and the translation of the cell-cycle regulatory protein. The use of the human cytomegalovirus promoter has proven to be advantageous. (Further examples for promoters are: Rous sarcoma virus long terminal repeat, SV 40 promoters, mouse mammary tumor virus LTR, metallothionein promoter, thymidin kinase promoter). The use of polyadenylation sequences and introns of the simian virus 40, of the gene for the bovine growth hormone and of the thymidin kinase gene have proven to be advantageous. Methods for the insertion of the constructs include lipofection, electroporation, transfection, and others.

Another possibility for increasing the intracellular concentration of a cell-cycle regulatory protein a direct insertion of corresponding mRNA into the cells via liposomes, lipofection or by electroporation, or by other methods suited for this purpose.

Another possibility is the insertion of a cell-cycle regulatory protein which was produced synthetically or in another organisms (i.e. bacteria, yeasts or other animal cells) into animal cells via liposomes or by other methods suited for this purpose.

In order to carry out the invention presented here the method of cultivation of the animal cells in serum-free and protein-free medium is of crucial importance. Animal cells which have been treated in a way that their intracellular concentration of a cell-cycle regulatory protein is increased in at least one phase of the cell-cycle are transferred from a serum-containing and protein-containing environment into a serum-free and protein-free culture medium. A serum-containing and protein-containing environment is either a serum-containing or protein-containing medium or a location in a whole animal. The serum-free and protein-free culture medium is characterized by the presence of all low molecular weight nutrients which are required for proliferation of the particular cell type. In addition to the nutrients that are normally included in commercially available culture media (as Dulbecco's modified Eagle's minimal essential medium DMEM or the minimal essential medium alpha, MEMalpha), it has proven essential that additional components such as iron and biotin necessary for biomass synthesis be added to the medium. For example, for CHO cells it is essential that iron salt (for example $FeSO_4$), linoleic acid, biotin and aspartic acid or asparagine be present in the medium.

It has proven to be advantageous that iron is present in concentrations around 0.6 mg/l (as ferrous iron), linoleic acid in concentrations around 0.007 mg/l and biotin in concentrations around 0.01 mg/ml. Asparagine or aspartic acid should be present in the range of 100 mg/l. These concentrations may strongly vary among cell types and basal medium formula used; these concentrations must be optimized for each cell type as is the case for all other substances in the medium formulation.

Dependent of the cell type, the addition of other substances may be essential or at least desirable. CHO cells for example proliferate in a medium which additionally contains putrescin, zinc, and thioctic acid as well as vitamin B12. CHO cells which are deficient in the dehydrofolate reductase gene will require hypoxanthine and thymidine. A culture medium which has proven to be advantageous for the growth of CHO cells, BHK 21 cells, HeLa cells as well as primary rat bone marrow cells is the FMX-CHOMaster medium of the company Dr. Messi Cell Culture Technologies, Zurich (described in the Ph.D. thesis ETH No. 9559 as FMX-8). The formulation of FMX-8 medium appears in Table 1 below.

TABLE 1

| MEDIUM COMPONENT | CONCENTRATION (mg/l) |
|---|---|
| Anorganic Salts | |
| $CaCl_2.2H_2O$ | 56.66 |
| $CoCl_2.6H_2O$ | — |
| $CuSO_4.5H_2O$ | — |
| $FeSO_4.7H_2O$ | 3.11 |
| KCl | 199.10 |
| $KH_2PO_4$ | — |
| $MgCl_2.6H_2O$ | — |
| $MgSO_4.7H_2O$ | 158.38 |
| $MnSO_4.H_2O$ | — |
| NaCl | 6955.00 |
| $NaHCO_3$ | 2100.00 |
| $Na_2HPO_4$ | 182.30 |
| $(NH_4)_6Mo_7O_{24}.4H_2O$ | — |
| $ZnSO_4.7H_2O$ | 0.74 |

TABLE 1-continued

| MEDIUM COMPONENT | CONCENTRATION (mg/l) |
|---|---|
| Other components | |
| D-Glucose | 1700.00 |
| Glutathion | — |
| Hypoxanthine | 10.00 |
| Linoleic acid | 0.07 |
| Thioctic acid | 0.18 |
| Phenol red | 2.67 |
| Putrescine | 0.27 |
| Na-pyruvate | 91.67 |
| Thymidine | 2.00 |
| Aminoacids | |
| L-Ala | — |
| L-Arg HCl | 188.33 |
| L-Asn $H_2O$ | 127.42 |
| L-Asp | — |
| L-Cis HCl $H_2O$ | 44.00 |
| Cystine | — |
| L-Gln | 87.50 |
| L-Glu | — |
| Gly | 14.58 |
| L-His HCl $H_2O$ | 46.29 |
| L-Ile | 22.35 |
| L-Leu | 57.75 |
| L-Lys HCl | 70.42 |
| L-Met | 18.11 |
| L-Phe | 18.71 |
| L-Pro | 37.08 |
| L-Ser | 13.13 |
| L-Thr | 44.84 |
| L-Trp | 25.11 |
| L-Tyr | 23.72 |
| L-Val | 61.74 |
| Vitamins | |
| Ascorbic acid | — |
| Biotin | 0.01 |
| Ca-pantothenate | 2.83 |
| Choline chloride | 45.00 |
| Folic acid | 2.33 |
| Myo-inositol | 15.17 |
| Niacinamide | 1.98 |
| Pyridoxine HCl | 2.18 |
| Riboflavin | 0.40 |
| Thiamine HCl | 1.46 |
| Vitamin $B_{12}$ | 0.88 |

It may be necessary for some cell types that the cell culture plastic is coated in advance with adhesive substances.

Of course a culture able to proliferate in protein-free medium will also proliferate in media in which certain proteins are added. Our invention includes such cases and is not restricted to cultures or methods in which only protein-free medium is used.

The invention presented here offers the possibility to grow cells that are originally surface dependent in a fully suspended state. For example, overexpression of cyclin E enabled CHOK1 cells to grow in a fully suspended state.

One of the advantages of the invention presented here is the short time requirements for the transition of animal cells to serum- and protein-free growth compared to other methods involving adaptation or random mutation and selection. Cells that are already in use in a production process could be engineered to grow in serum-free and protein-free medium without a long process of adaptation in which some desirable properties might be lost.

The time requirements that are necessary for the transition to serum-free and protein-free growth using methods of the present invention are in the range of a few weeks. The usual transition is here below described for the frequently used CHO K1 cells. The cell line is e.g. transfected with an expression vector for cyclin E. A suitable method for this purpose is lipofection. One day after transfection the cells can be transferred into e. g. a T-25 flask which is coated with fibronectin. After trypsinization the cells preferably are taken up into a solution of 1 mg / ml soybean trypsin inhibitor in FMX-8 medium. From this solution the cells are transferred into 6 ml of FMX-8 medium in a T-25 flask. After 7 to 10 days the culture can be transferred into a T-75 flask and after an additional 7–10 days into a T-150 flask. Different splitting ratios are preferably applied in order to insure the optimal performance of the cultures (e.g. ½–1/40) When late exponential growth phase is reached in this culture can alternatively be further cultivated as adherent cultures in T-flasks with splitting ratios of 1/40 per week or as suspended cultures in spinner flasks or in bioreactors. The transfected cells offer the opportunity to be cultured either in suspension or adherent on a surface. In the case of CHO K1 cells the use of the cDNA for cyclin E has proven to be advantageous. Experiments with CHO cells in which the expression vector E2F was overexpressed were successful as well, but the properties of these cells were surpassed by the cyclin E-overexpressing cells.

Cyclin E-overexpressing CHO cells display excellent growth parameters. The specific growth rate $\mu$ in a spinner culture as described above is 0.8 $d^{-1}$, which is in the range of the highest values reported for CHO cell lines that have been obtained by an extended adaptation process. The requirements for initial cell densities are much lower in the cyclin E-overexpressing cell line than in other protein-free growing cell lines. For the cyclin E-expressing cells, 5000 cells/ml are sufficient for inoculation, the cells immediately entered the exponential growth phase. This means that fewer intermediate culture vessels are required for an industrial scale process. Cells can be transferred directly from a relatively small reactor into a large vessel. The handling of the process is strongly simplified by this favorable characteristic of the CHO K1: cyclin E cells. The invention will be described in more details in the examples that will follow.

EXAMPLE 1

Cloning of the human cyclin E cDNA and expression in CHO K1 cells

The cDNA of human cyclin E can be isolated from a HeLa CDNA library by standard hybridization techniques. All the following methods are standard laboratory techniques and have been carried out according to Sambrook et al. (Sambrook, J., Fritsch, E. F. and Maniatis, T. Molecular cloning, Cold Spring Harbour Laboratory Press (1989)). HeLa mRNA was isolated with the aid of an mRNA extraction kit from Pharmacia. The CDNA of cyclin E was isolated by standard hybridization techniques according to Sambrook et al. cDNA synthesis and ligation of the CDNA fragments into lambda vector arms was carried out with the aid of a lambda cDNA cloning kit (Stratagene). After in vivo excision ("zapping") of the lambda vector according to the manufacturer's guidelines the cDNA of cyclin E was part of the plasmid pBluescript. A 2.5 kb fragment could be isolated on a 0.8% low melting agarose gel after digestion of the plasmid with the restriction enzyme Eco Rl. After linearization of the vector pRc/CMV (Invitrogen) with the restriction enzyme Bst X1, the sticky ends of the vector and the cDNA fragment were. filled in with the Klenow enzyme to yield double blunt-ended linear DNA fragments. Large quantities of the expression vector were produced with the aid of the Flexi prep™ kit of Pharmacia after ligation and transformation of the product into the *E. coli* strain DH5 alpha and identification of a construct in the sense orientation.

CHO K1 were seeded into a six well plate (Falcon) in a manner that the cell density reached about 50% of confluence at the day of transfection. The medium used contained 10% of fetal calf serum (FCS); (Ham's F12 +10% FCS).

Lipofection was carried out as described by the manufacturer of the reagent Lipofectamin (Gibco BRL). 10 $\mu$l Lipofectamin and 1–2 $\mu$g of the expression vector were mixed as described in the manual and incubated for 1 h. 1 ml of this mixture was added to the cells that had been washed three times in advance with serum-free FMX-8 medium. 1.5 ml of FMX medium supplemented with 10% FCS was added after 6 h, and the cells were incubated another 18 h at 37° C. and in 5% $CO_2$ in air.

24 h after lipofection the cells were trypsinized. The detached cells were taken up in a solution of 1 mg / ml soybean trypsin inhibitor (Sigma) in FMX-8 medium. The first three weeks after transfection the cells were cultured in T-flasks that were coated with 1 $\mu g/cm^2$ fibronectin (Boehringer Mannheim). Since the efficiency of lipofection and the degree of surviving cells may vary strongly, it is advisable to seed the cells in different concentrations after each splitting (ratios of ½ to 1/20). Proliferation will continue also for some days in the nontransfected cells and to a higher degree in the cells that are only transiently transfected after removal of the serum from the culture. In the subsequent two to three weeks the stable clones that overexpress cyclin E will overgrow the culture. It is important that the cells are subcultured weekly into new T-flasks, since growth inhibition may occur due to products from dead and lysed cells. It is not important whether the cells have reached confluency or not before transfer to a new flask.

Figure 3:
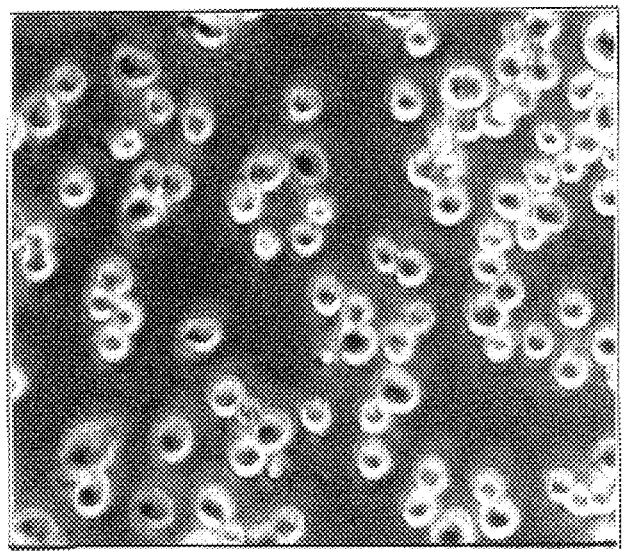
FIG. 3 shows the morphology of cyclin E-overexpressing cells in T-flask culture. CHO Kl cyclin E cells rounded up and finally grew fully in suspension.
Figure 4:
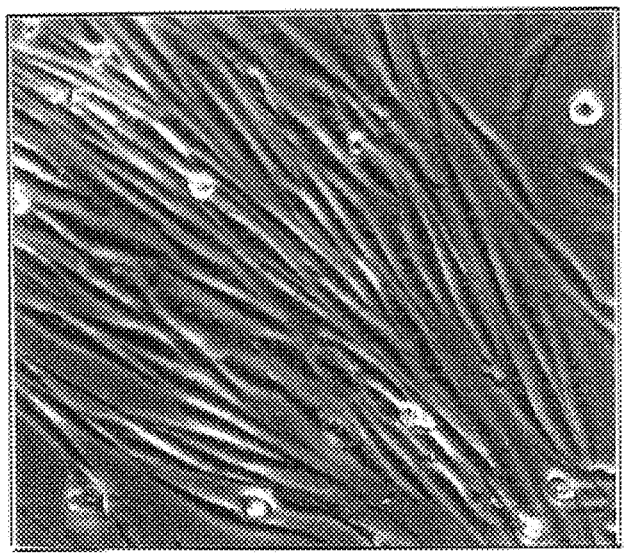
FIG. 4 shows the morphology of untransfected CHO K1 cells in FMX 8 medium. The control cells had the same morphology as in serum-containing culture. They entered a quiescent state and remained attached to the substratum.

After one week the culture was transferred into a coated T-75 flask and, after three further weeks with splitting ratios between ½ and 1/20, the cells could be cultivated with weekly splitting ratios of 1/40 in uncoated T-flasks. It is advantageous to apply different splitting ratios at each subculture during the first four weeks when the transfected and growing cells are selected. This insures the survival of the culture during this critical phase. CHOK1:cyclinE cells so selected have been maintained in culture for six months with weekly splitting ratios maintained at 1/40. Control cells that have been transfected with the empty vector or that have been subjected to mock transfections stopped growing and died in the course of the first two weeks. FIG. 1 shows the increased cyclin E expression of the new cell line CHO K1:cycE that has the ability to grow well in serum-free and protein-free FMX-8 medium. Control cultures did not express cyclin E under the same conditions. FIG. 3 shows the morphology of CHO k1:cycE cells and FIG. 4 shows the untransfected parental cell line CHO K1 in the same protein free medium.

EXAMPLE 2

Growth of cyclin E-overexpressing CHO K1 cells in suspension culture

CHO k1:cycE cells were cultivated in spinner flasks four weeks after transfection. CHO k1:cycE cells were trypsinized and subsequently taken into a 1 mg/ml solution of soybean trypsin inhibitor. After centrifugation, the cells were taken up into serum-free and protein-free FMX-8 medium. The cultivation parameters were as follows: working volume: 0.5 l, medium: FMX-8, 37° C., 5% $CO_2$ in air, 40 rpm around 720°. The inoculum consisted of 3·10⁶ cells in 50 ml of fresh medium. The initial cell density was 6'000 cells /ml.

Figure 2:
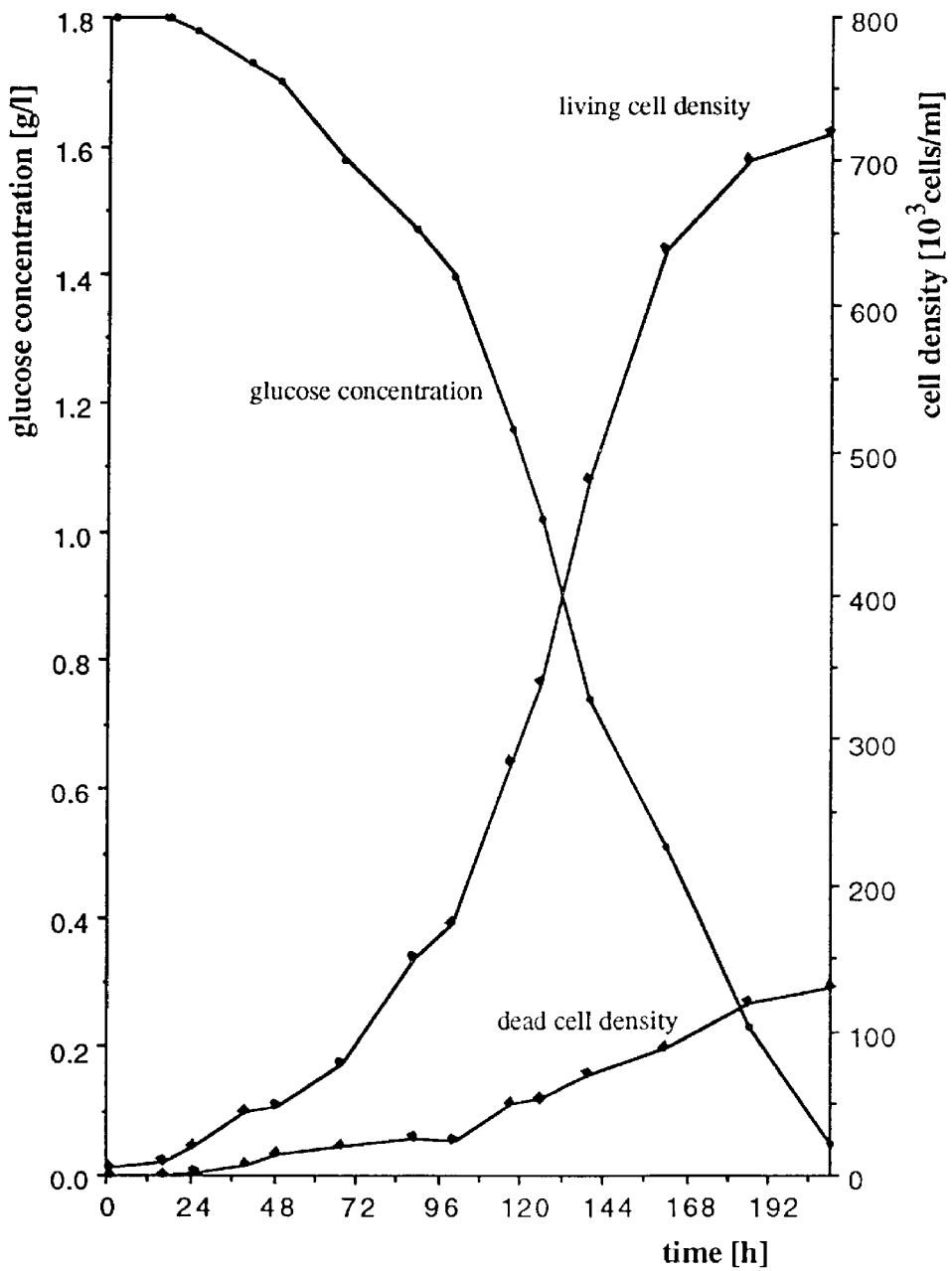
FIG. 2 shows living and dead cell density and glucose concentration of a spinner cultivation of CHO K1 cyclin E cells, in serum- and protein - free medium (working volume 0.5 1, medium: FMX-8 (described in the Ph.D.. thesis F. Messi ETH No. 9559), 37° C., 5% $CO_2$ in air, 40 rpm rotation around 720°, Inoculum: $3·10^6$ cells in 50 ml of fresh FMX-8, initial cell density $6·10^3$ cells/ml, maximal living cell density: $7.2·10^5$ cells/ml, $\mu$max=0.8 $d^{-1}$).

An advantage of the CHO k1:cycE cell line is its ability to proliferate without autocrine stimulation. This results in an extreme low inoculum requirement of this cell line. This is advantageous for inoculation of large culture vessels. FIG. 2 shows a growth curve of CHO k1:cycE cells.

EXAMPLE 3

Cloning and expression of the transcription factor E2F in CHO K1 cells

Figure 5:
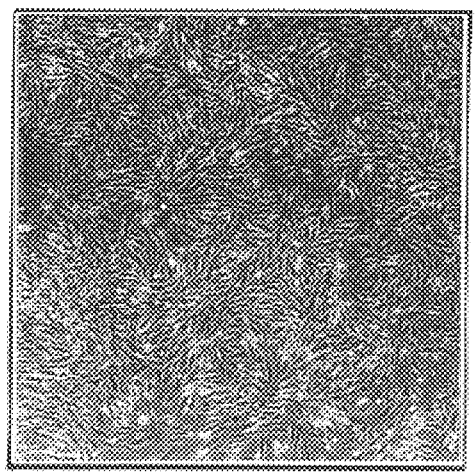
FIG. 5 shows CHO K1 cells transfected with an expression vector for the transcription factor E2F-1 and FIG. 6 shows CHO K1 that were transfected with the empty pRc vector.
Figure 6:
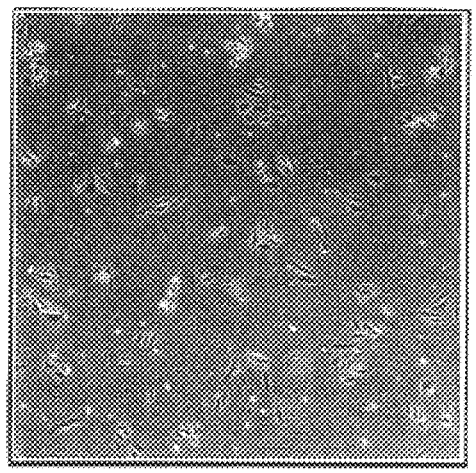

The cDNA of the transcription factor E2F-1 was isolated from a HeLa cDNA library as described in Example 1. A 1.6 kb fragment which contained the entire coding sequence was cleaved from pBluescript with the restriction enzymes Xba 1 and Hind III. After isolation on a 0.8 % low melting agarose gel, the fragment was ligated in sense orientation into the pRc/CMV vector which was previously digested with the restriction enzymes Xba 1 and Hind III. 1–2 µg of this expression vector were transfected into CHO K1 cells as described in Example 1. CHO k1:E2F cells showed a clearly prolonged period of fast growth after serum removal compared to control cells (cf. FIG. 5 and FIG. 6). The cells underwent at least 6 further rounds of division before the growth rate slowed down.

EXAMPLE 4

Cloning and stable expression of the transcription factor E2F-1 in CHO K1 cells

The cDNA of the transcription factor E2F-1 was isolated from a HeLa cDNA library as described in Example 1. A 1.6 kb fragment which contained the entire coding sequence was cleaved from pBluescript with the restriction enzymes XbaI and HindIII. After isolation on a 0.8% low melting agarose gel, the fragment was ligated in sense orientation into the pRc/CMV vector, which was previously digested with the restriction enzymes XbaI and HindIII.

Figure 7:
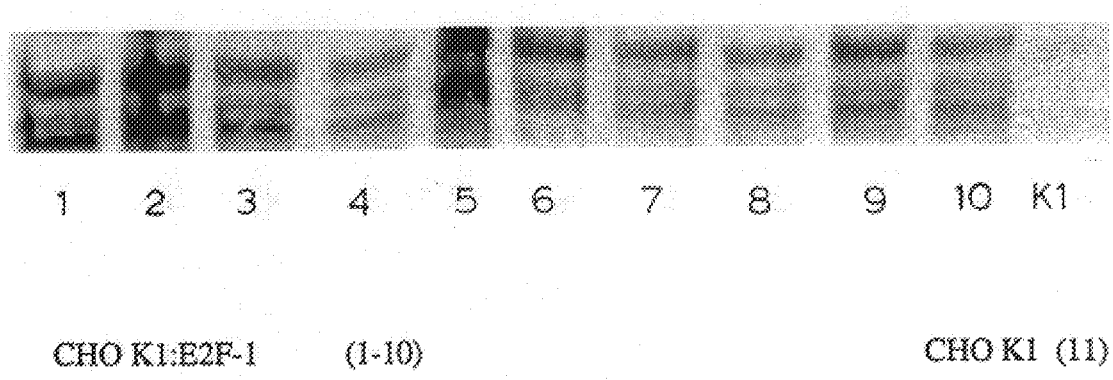
FIG. 7 shows a Western blot of 10 CHO K1:E2F-1 clones, as well as of the original CHO K1 cell line.

5 µg of DNA was transfected into CHO K1 cells in the presence of 10% FCS with the aid of DOTAP (Boehringer) according to manufacturer's instructions. After 5 days, the cells were exposed to 400 µg of neomycin. After approximately 10 more days, the CHO K1 control cells died. At this time, cells were diluted into 2 24-well plates with conditioned media+400 µg/ml neomycin for selection. The media were replaced every 3 days and after 20 days, 10 single clones were selected and preserved for further analysis. Western analysis reveals significantly more E2F-1 expressed in all 10 clones as compared with CHO K1 grown on FMX-8+10% FCS (see FIG. 7)

The k1:E2F-1 clones were grown up in the presence of 10% FCS, washed three times with protein-free FMX-8 and subsequently split into 6 well plates containing protein-free FMX-8 at seeding densities of 25,000, 50,000, and 100,000 cells per well. In the presence of 1% or 0% serum, the cells were able to proliferate. Furthermore, k1:E2F-1 cells that were grown in the presence of 1% serum and subsequently split as above into 0% serum also exhibited growth in a protein-free environment. In all cases tested various concentrations of neomycin and low serum concentration (<1%) or completely serum- and protein-free medium, the k1:E2F-1 cells were able to proliferate, while CHO K1 control cells died. CHO k1:E2F-1 displayed a spread moprphology, even on uncoated cell culture plastic (see FIG. 5).

While there are shown and described present preferred embodiments of the invention, it is to be distinctly understood that the invention is not limited thereto, but may be otherwise variously embodied and practiced within the scope of the following claims.

What we claim is:

1. An animal cell which is transfected with an exogenous nucleic acid sequence encoding a cyclin E protein or an E2F transcription factor and which expresses said protein at a level which allows the cell to proliferate in serum-free and protein-free culture media.

2. The cell of claim 1 which is transfected with at least one exogenous nucleic acid sequence encoding a cell-cycle regulatory protein, wherein said at least one nucleic acid sequence is selected from the group consisting of a nucleic acid sequence encoding a cyclin E protein, a nucleic acid sequence encoding an E2F transcription factor, and a mixture of such nucleic acid sequences.

3. The cell of claim 1, wherein the culture medium contains iron, linoleic acid, biotin and asparagine or aspartic acid.

4. The cell of claim 1, wherein the cell contains intracellularly at least one exogenous nucleic acid sequence encoding a substance to be produced.

5. The cell of claim 1, wherein the animal cell is a CHO cell.

6. The cell of claim 2, wherein said at least one nucleic acid sequence is a nucleic acid sequence encoding cyclin E.

7. The cell of claim 2, wherein said at least one nucleic acid sequence is a nucleic acid sequence encoding the transcription factor E2F- 1.

8. The cell of claim 2, wherein said at least one nucleic acid sequence comprises a nucleic acid sequence encoding cyclin E and a nucleic acid sequence encoding transcription factor E2F-1.

9. The cell of claim 3, wherein the culture medium furthermore contains at least one component selected from the group consisting of putrescin, zinc and vitamin B12.

10. The cell of claim 3, wherein the culture medium furthermore contains putrescin, and zinc, and vitamin B12.

11. A mammalian cell which is transfected with an exogenous nucleic acid sequence encoding a cyclin E protein or an E2F transcription factor and which expresses said protein at a level which allows the cell to proliferate in serum-free and protein-free culture media.

12. The cell of claim 11 which is transfected with at least one exogenous nucleic acid sequence encoding a cell-cycle regulatory protein, wherein said at least one nucleic acid sequence is selected from the group consisting of a nucleic acid sequence encoding a cyclin E protein, a nucleic acid sequence encoding an E2F transcription factor, and a mixture of such nucleic acid sequences.

13. The cell of claim 11, wherein the culture medium contains iron, linoleic acid, biotin and asparagine or aspartic acid.

14. The cell of claim 11, wherein the cell contains intracellularly at least one exogenous nucleic acid sequence encoding a substance to be produced.

15. The cell of claim 11, wherein the mammalian cell is a CHO cell.

16. The cell of claim 12, wherein said at least one nucleic acid sequence is a nucleic acid sequence encoding cyclin E.

17. The cell of claim 12, wherein said at least one nucleic acid sequence is a nucleic acid sequence encoding the transcription factor E2F-1.

18. The cell of claim 12, wherein said at least one nucleic acid sequence comprises a nucleic acid sequence encoding cyclin E and a nucleic acid sequence encoding transcription factor E2F-1.

19. The cell of claim 13, wherein the culture medium furthermore contains a member selected from the group consisting of putrescin, zinc and vitamin B12.

20. The cell of claim 13, wherein the culture medium furthermore contains putrescin, and zinc, and vitamin B12.

21. An animal cell which is transfected with an exogenous nucleic acid sequence encoding a cyclin E protein or an E2F transcription factor and which expresses said protein at a level which allows the cell to proliferate in serum-free and protein-free culture media, said cell produced according to the method wherein said exogenous nucleic acid sequence is introduced into an animal cell which grows in a serum-containing and protein-containing environment, the serum-containing and protein-containing environment being replaced by an at least serum-free environment before, at the time of, or after the introduction of said exogenous nucleic acid sequence.

22. The cell of claim 21, wherein an adhering culture is converted into a suspended one.

23. The cell of claim 21 wherein the cell, which originally grows exclusively in a serum-containing and protein-containing environment, contains at least one exogenous nucleic acid sequence encoding a substance to be produced.

24. The cell of claim 21 wherein a nucleic acid sequence encoding a substance to be produced is introduced into the cell, which is able to proliferate in serum-free and protein-free media.

25. A mammalian cell which is transfected with an exogenous nucleic acid sequence encoding a cyclin E protein or an E2F transcription factor and which expresses said protein at a level which allows the cell to proliferate in serum-free and protein-free culture media, said cell produced according to the method wherein said exogenous nucleic acid sequence is introduced into a mammalian cell which grows in a serum-containing and protein-containing environment, the serum-containing and protein-containing environment being replaced by an at least serum-free environment before, at the time of, or after the introduction of said exogenous nucleic acid sequence.

26. The cell of claim 25 wherein an adhering culture is converted into a suspended one.

27. The cell of claim 25 wherein the cell, which originally grows exclusively in a serum-containing and protein-containing environment, contains at least one exogenous nucleic acid sequence encoding a substance to be produced.

28. The cell of claim 25 wherein a nucleic acid sequence encoding a substance to be produced is introduced into the cell, which is able to proliferate in serum-free and protein-free media.

* * * * *